United States Patent [19]

Wiersum et al.

[11] Patent Number: 5,032,400

[45] Date of Patent: Jul. 16, 1991

[54] SHARK LIVER OIL AND GARLIC OIL TOPICAL ANALGESIC

[75] Inventors: Jeffery Wiersum; Henry E. Troy, both of Syracuse, N.Y.

[73] Assignee: Erie Laboratories, McLean, Va.

[21] Appl. No.: 430,353

[22] Filed: Nov. 2, 1989

[51] Int. Cl.$^5$ .................. A61K 35/78; A61K 35/60; A61K 35/407

[52] U.S. Cl. ................. 424/195.1; 514/825; 424/523; 424/553; 424/554

[58] Field of Search ............ 424/554 F, 553 F, 523 F, 424/524; 514/825 F, 783

[56] References Cited

U.S. PATENT DOCUMENTS

| | | | |
|---|---|---|---|
| 445,995 | 2/1891 | Hebert | 424/523 |
| 1,058,643 | 4/1913 | Tahara | 424/554 |
| 2,320,479 | 6/1943 | Sperti | 424/553 |
| 2,437,561 | 3/1948 | Schaaf | 424/195.1 |
| 2,618,561 | 7/1952 | Spinra et al. | 99/140 |
| 3,227,616 | 7/1966 | VanWessem et al. | 167/91 |
| 3,629,409 | 4/1971 | Gregory | 424/195 |
| 4,241,048 | 11/1980 | Durbak et al. | 424/45 |
| 4,296,104 | 10/1981 | Herschler | 424/153 |
| 4,521,411 | 10/1985 | Koloff | 424/195.1 |
| 4,572,915 | 2/1986 | Crooks | 514/458 |
| 4,647,586 | 3/1987 | Mizushima | 514/532 |
| 4,788,061 | 11/1988 | Shore | 424/448 |
| 4,795,636 | 1/1989 | Tsuei | 424/195.1 |
| 4,816,271 | 3/1989 | Scaffidi | 424/60 |
| 4,895,727 | 1/1990 | Allen | 424/642 |

OTHER PUBLICATIONS

The Merck Index, 9th Ed., 1976, Pub. by Merck, pp. 42, 1128, Bennett, Chemical Formulary 1933-4, vol. I, Pub. by the Chemical Formulary, 950 Third Ave., Brooklyn, N.Y.

*Primary Examiner*—Johnnie R. Brown
*Assistant Examiner*—R. Gitomer
*Attorney, Agent, or Firm*—Nixon & Vanderhye

[57] ABSTRACT

Strains, sprains and sore skeletal muscles are treated with topical application of pharmaceutical composition containing a combination of shark liver oil and garlic oil in a cream or ointment base.

2 Claims, No Drawings

SHARK LIVER OIL AND GARLIC OIL TOPICAL ANALGESIC

BACKGROUND OF THE INVENTION

This invention relates to analgesic compositions and methods of using them for therapeutic benefit.

Castor oil has been applied over painful areas of the body to reduce pain and inflammation. The oil instilled into a cotton flannel cloth and placed over the painful joint, tendon, nerve trunk and covered with Saran wrap is used to form an occlusive dressing. Thick turkish towelling is placed over the Saran wrap and covered with an electric heating pad, in turn kept in place by an outside towel. Under low heat, this stupe is kept on, immobilizing the patient for at least an hour twice daily. The method is effective but cumbersome, time consuming and interferes with other activities while thus engaged.

We have studied combinations of other natural oils plus excipients which were compatible with each other, safe enough to be edible, readily available and inexpensive, aiming for the over the counter market to make an anti-inflammatory treatment affordably available to the maximum number of suffering individuals. Hundreds of combinations of oils and excipients were tried, many of them laboratory failures and the others no more effective than the castor oil in stupe form, our aim being to use the product topically with no wrapping or other treatment other than topical application.

Medical literature reports the virtues of garlic and shark liver oils separately as effective anti-inflammatory agents. The active ingredients of garlic and shark liver oils have been successfully used in ancient Chinese herbal medical practice, although the manufacturing process is not known. Both garlic oil and shark liver oil separately have been reported for years in foreign, especially oriental medical journals, as being effective in inflammatory and infective illnesses. In recent American literature, the antiviral activity of garlic oil has been reported. We added these two oils to others we had previously tried and began to see improved results. Finally, when serendipitously supplied with a refined grade of shark liver oil and combining all of the ingredients under special conditions of temperatures and times, the resulting formulations produced uniformly and unexpected results in many conditions and diseases the nature of which continue to be discovered.

DESCRIPTION OF THE INVENTION

This invention relates to topical analgesics and pharmaceutical preparations causing increased circulation to the skin and its counterpart in deeper body structures. These preparations are used to relieve pain from the skin and, more importantly, surrounding tissue and bone structures as well as other uses. The pharmaceutical compositions of this invention are prepared for topical application to a painful or inflamed area, particularly for relieving the pain of inflammatory skeletal diseases and related disorders including arthritis, bursitis, neuritis, sprains, strains, exercise-induced joint pain of unknown etiology and the like.

The compositions of this invention are characterized by the presence of three or more oils together in therapeutic quantities. The oils are garlic oil, shark liver oil and soybean oil. These oils are formulated, together with emulsifiers, fragrances and other ingredients into a pharmaceutically elegant preparation for topical application, which is an ointment or preferably a cream.

Garlic oil or allium oil, prepared from the fresh bulbs of *Allium sativum*, is a yellowish volatile oil containing various sulfur compounds. Untreated, it has a rather strong, unpleasant odor as might be expected. The garlic oil used in the pharmaceutical preparations of this invention is significantly masked by fragrance. Shark liver oil or shark oil, extracted from the livers of various species of shark, contains significant quantities of Vitamin A and has been used in Vitamin A therapy. It contains aqualene, a biochemical precursor of cholesterol, and has been used as a constituent in therapeutic preparations or emulsified as an emollient for its moisturizing properties.

The preferred compositions of this invention are emulsions having an oil phase dispersed with suitable emulsifiers and stabilizers into an aqueous phase. The selection of oils for the oil phase, in addition to garlic oil and shark oil, will be determined by the desired volume of the oil phase, for which soybean oil or a similar "neutral" oil may be used, and for the overall fragrance and presentation of the composition, for which almond oil or other volatile oil of compatible and acceptable fragrance may be used. The oil phase may include emulsifying agents, notably emulsifying wax N.F., a waxy solid prepared from cetostearyl alcohol containing a polyoxyethylene derivative of a fatty acid and its salts, a mixture of stearic and palmitic acids, commonly used as a base in ointments, creams and cosmetics.

Other fat sources used as emollients in cream bases include myristic acid, its esters and alcohols. Antioxidants, such as alpha tocopherol (Vitamin E) or the like used as antioxidants for plant and animal oils, protectives, stabilizers, preservatives and the like may be incorporated as well. Preferably, the topical analgesic preparations of this invention are composed of ingredients each of which are individually edible.

The aqueous phase of the emulsion contains primarily water, such as distilled or deionized water, and a compatible, water-soluble humectant, such as propylene glycol, together with emulsifiers and dispersants.

To the prepared emulsion fragrance, colorings and other ingredients may be added as desired.

The topical analgesic formulations of this invention are applied to the skin in the area of discomfort and/or inflammation and are recommended for conditions such as joint stiffness and pain or areas of benign skin eruptions for temporary relief. Preferably the topical composition is applied at night and wrapped or otherwise covered to protect clothing and bedding. Daily application is continued until relief is achieved for up to one week or longer. Applications may then discontinued and resumed should pain or discomfort reappear.

The invention will be further explained by reference to the following example which is offered by way of illustration and not limitation. All parts and percentages are by weight unless otherwise indicated.

EXAMPLE

A. The following ingredients were mixed together in the order listed and in the amounts indicated:

|  | % by weight |
| --- | --- |
| emulsifying wax N.F. XVII | 1–8 |
| garlic oil | 0.05–0.5 |
| stearic acid | 1–3 |

-continued

|  | % by weight |
|---|---|
| shark liver oil | 2-12 |
| almond oil | 2-8 |
| myristylmystate | 0.5-2 |
| soybean oil | 2-10 |
| propyl paraben | 0.05-0.5 |
| alpha tocopherol | 1-6 |

The resulting mixture was heated to 80° C.

B. In a separate container, the following ingredients were mixed also in the order listed in the quantities indicated:

|  | % by weight |
|---|---|
| distilled water | 40-70 |
| Acrysol ICS-1 | 0.1-0.8 |
| propylene glycol | 2-8 |
| methyl paraben | 0.05-0.6 |
| diazolidinyl urea and parabens | 0.05-0.6 |
| triethanolamine 99% | 0.5-2.5 |

This mixture was heated to 90° C.

The heated mixtures from parts A and B were mixed with each other slowly with rapid agitation until mixing was complete and the resulting product was uniform. The product of A and B was then cooled to 40° C.

C. In a separate container the following ingredients are mixed in the order and listed and in the amounts indicated:

|  | % by weight |
|---|---|
| soluble reticulin | 0.05-2 |
| hydrolyzed elastin | 0.5-2 |
| Alpine fragrance 161-742 | 0.1-6 |

The individual ingredients, 18 in all, total 100%. Soluble reticulin is a collagen compound which forms a network to build up connective tissue. It cooperates with elastin in the major elastic protein of collagen. Acryosol ICS-1 is an alkali soluble acrylic polymer emulsion.

The mixture from part C was added to the product of A and B mixed until uniform then cooled to room temperature. The final product was a tan colored, creamy oliganeous semi-solid resembling face cream with a slightly peach smell and a pH of between 7.5 and 8.0. It was packaged in one ounce metal tubes.

The pharmaceutical composition of this invention, when topically applied to the affected area, provides relief of pain, stiffness, soreness and swelling in both shallow and deep body tissues and thus is indicated for use in the temporary treatment of inflammatory skeletal muscle conditions arthritis, bursitis, neuritis, strains, sprains, and other sports injuries or other conditions amenable to topical application when relief is needed. Other uses for these compositions are described above and will be apparent to the reader. Methods of effecting topical analgesia, treating inflammation and treating viral infections are also within our invention.

We claim:

1. A method of effecting topical analgesia in a person needing same comprising topically applying to the affected surface of the body of said person an effective amount of a topical analgesic composition consisting essentially, in parts by weight, of:

|  |  |
|---|---|
| shark liver oil | 2-12 |
| garlic oil | 0.05-0.5 |
| almond oil | 2-8 |
| soybean oil | 2-10 |
| pharmaceutically acceptable cream or ointment base | balance. |

2. The method of claim 1, in which the analgesic composition is applied to the affected surface of the patient's body one to four times per day.

* * * * *